United States Patent [19]
Weintraub et al.

[11] Patent Number: 5,120,840
[45] Date of Patent: Jun. 9, 1992

[54] 4-AMINO-4-ENE-STEROIDS AND THEIR USE AS 5α-REDUCTASE INHIBITORS

[75] Inventors: Philip M. Weintraub, Cincinnati; Joseph P. Burkhart, West Chester; Thomas R. Blohm, Maderia, all of Ohio

[73] Assignee: Merrell Dow Pharmaceuticals Inc., Cincinnati, Ohio

[21] Appl. No.: 720,900

[22] Filed: Jul. 2, 1991

Related U.S. Application Data

[63] Continuation-in-part of Ser. No. 561,041, Aug. 1, 1990, and a continuation-in-part of Ser. No. 671,555, Mar. 19, 1991.

[51] Int. Cl.$^5$ .................... C07J 17/00; C07J 41/00
[52] U.S. Cl. ........................... 540/94; 552/515; 540/28
[58] Field of Search ................... 552/515; 540/94

[56] References Cited

U.S. PATENT DOCUMENTS 3,637,668  1/1972  260 ........................ 239.5/
3,780,070  12/1973  Shapiro ................ 260/349

FOREIGN PATENT DOCUMENTS 0260975  9/1987  European Pat. Off. ............ 552/515
0286578  3/1988  European Pat. Off. ............ 552/515
0291290  5/1988  European Pat. Off. ............ 552/515
2171100  2/1986  United Kingdom ................ 552/515

OTHER PUBLICATIONS

R. D. Lynch, "Synthesis and Chemistry of Steroidal Azido Ketones. Possible Photoaffinity Labels for Steroids Receptor Proteins," Ph.D. Dissertation (Vanderbilt University), Dec. 1977, pp. xiv, xv, 22,26,40,41,42,95 and 96.
Ekhato et al., *J. Chem. Soc. Perkin Trans. I*, 1988, 3239.
*Chemical Abstracts*, 64, 2142e (1966).
Derwent Basic Abstract 9186 (JP 17673/63).
Derwent Basic Abstract 11,765 (JP 4476/64).

*Primary Examiner*—Werren B. Lone
*Assistant Examiner*—Kimberly J. Kestler
*Attorney, Agent, or Firm*—John J. Kolano

[57] ABSTRACT

The present invention relates to 4-amino-Δ$^4$-steroids which are useful as inhibitors of 5α-reductase. The compounds are prepared by the reaction of an appropriate 4-azido steroid with triphenylphosphine in an aqueous inert solvent with heating.

9 Claims, No Drawings

4-AMINO-4-ENE-STEROIDS AND THEIR USE AS 5α-REDUCTASE INHIBITORS

The present application is a continuation-in-part of application Ser. No. 561,041, filed Aug. 1, 1990 and application Ser. No. 671,555, filed Mar. 19, 1991.

BACKGROUND OF INVENTION

Mammalian steroid 5α-reductase, an enzyme present in mammalian tissues including skin, male genitalia and prostate gland, catalyzes the conversion of the steroidal hormone testosterone to the steroidal hormone dihydrotestosterone (17β-hydroxy-5α-androstan-3-one). Testosterone and dihydrotestosterone (DHT) are both androgenic hormones and they are the primary androgenic steroids in males. These steroids are responsible for the physical characteristics which differentiate males from females. DHT, however, is much more potent than testosterone as an androgen and it acts as an end-organ effector in certain tissues, particularly in mediating growth. Furthermore, the formation of DHT occurs primarily in the target cells themselves as a result of the reduction of testosterone by 5α-reductase.

It is known that skin responds to androgens and is an active site of androgen metabolism. In particular, testosterone is converted to DHT in the skin by the action of 5α-reductase. Testosterone metabolism in the skin may at times be abnormally excessive and have undesirable effects as a result of the DHT formed. Thus, there is considerable evidence that DHT is involved in the pathogenesis of acne, including acne vulgaris, as well as other androgen associated conditions [See Price, *Arch. Dermatol.* 111, 1496 (1975)]. Agents which are capable of blocking the formation of DHT from testosterone in skin, such as by inhibiting the activity of 5α-reductase, would therefore be useful in the treatment of acne.

In addition, other physical conditions and disease states, including benign prostatic hypertrophy, androgenic alopecia (common baldness caused by androgen in genetically susceptible men and women), seborrhea and female hirsutism, are also associated with elevated androgen activity and could be treated by the administration of 5α-reductase inhibitors. [See T. Liang et al., *Endocrinology* 117, 571 (1985); J. R. Brooks et al., *Steroids* 47, 1 (1986); J. R. Carlin et al., *Journal of Chromatography*, 427, 79 (1988).] Thus, agents which are capable of blocking the formation of DHT from testosterone by inhibiting the effects of 5α-reductase would also be effective in the treatment of these conditions.

DETAILED DESCRIPTION OF THE INVENTION

The present invention relates a group of compounds which are 4-amino-Δ⁴-steroids and to the use of these compounds as inhibitors of 5α-reductase. The invention further relates to certain novel 4-azidosteroids which serve as intermediates to the aminosteroids. More particularly, the present invention relates to aminosteroid compounds having the following general formula:

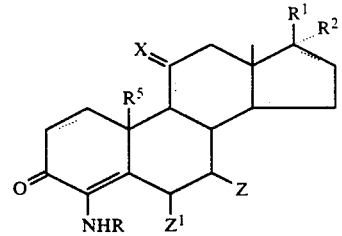

wherein R is hydrogen or $C_{1-4}$ alkyl; $R^1$ is $C_{2-6}$ alkanoyl, —($C_{1-6}$ alkyl)-$OZ^2$, —$C_{2-6}$ alkyl)—$(OZ^2)_2$ or —A—C(O)—Y; $Z^2$ is hydrogen, $C_{1-6}$ alkyl, phenyl-($C_{1-4}$ alkyl), ($Y^1$-substituted phenyl)-($C_{1-4}$ alkyl), $C_{1-6}$ alkanoyl, benzoyl or $Y^1$-substituted benzoyl wherein $Y^1$ is methyl, halogen or methoxy; A is absent or is present as an alkylene of 1 to 6 carbon atoms; Y is —OH, —O($C_{1-6}$ alkyl) or —$NR^3R^4$; $R^2$ is hydrogen or $R^1$ and $R^2$ can be combined to give —O—$CH_2CH_2CH_2$—; $R^3$ and $R^4$ are each independently hydrogen, $C_{1-6}$ alkyl, $C_{3-6}$ cycloalkyl or they can be combined to give —$(CH_2)_n$— wherein n is 4 to 6; $R^5$ is hydrogen or methyl; X is O or (H)(H); Z is hydrogen or $C_{1-6}$ alkyl; $Z^1$ is hydrogen or methylene; and each of the dotted lines in the rings indicates the optional presence of a double bond with the proviso that a 9,11-double bond can only be present when X is (H)(H) and the proviso that, when a 16,17-double bond is present, then $R^2$ is absent.

The various alkyl groups referred to above can be straight or branched-chain and can be exemplified, with the carbon limitations as provided, by methyl, ethyl, propyl, isopropyl, butyl sec-butyl, tert-butyl, pentyl and hexyl. When the alkyl groups are substituted by two —$OZ^2$ groups, the two $OZ^2$ groups are situated on different carbon atoms. Some examples of the two types of HO-substituted alkyl groups referred to above are hydroxymethyl, 1-hydroxyethyl, 1,2-dihydroxyethyl, 1-methyl-2-hydroxyethyl, 1-hydroxypropyl and 3-hydroxypropyl. Examples of etherified $R^1$ groups (i.e., $Z^2$ is alkyl or phenylalkyl) are 2-methoxy-1-methylethyl and 2-(penylmethoxy)-1-methylethyl. Examples of esterified $R^1$ groups (i.e., $Z^2$ is alkanoyl, benzoyl or substituted benzoyl) are 2-acetoxy-1-methylethyl and 2-benzoyloxy-1-methylethyl. In those cases where optical isomerism is possible in the $R^1$-substituent, the individual pure optical isomers are each part of this invention. Examples of the halogen substituents referred to above are fluorine, chlorine and bromine. The $C_{2-6}$ alkanoyl groups referred to above can be straight or branched-chained and can be exemplified by acetyl, propionyl, butyryl, isobutyryl and hexanoyl. The $C_{1-6}$ alkanoyl groups can be exemplified similarly and also include formyl. The $C_{3-6}$ cycloalkyl groups can exemplified by cyclopropyl, cyclobutyl, cyclopentyl and cyclohexyl. When $R^3$ and $R^4$ are combined to give —$(CH_2)_n$—, then —$NR^3R^4$ can be exemplified by 1-pyrrolidinyl, 1-piperidinyl or hexahydro-1H-azepin-1-yl. When $R^1$ is —A—C(O)—Y and A is absent, then the carbonyl function is attached directly to the steroid ring; when A is alkylene of 1 to 6 carbon atoms, examples of A are methylene, ethylene, ethylidene, propylene and tetramethylene. When $R^1$ and $R^2$ are combined as —O—$CH_2CH_2CH_2$—, a spirotetrahydrofuran structure results.

A preferred group of compounds are those in which $R^2$ is hydrogen and X is (H)(H). Further preferred are those compounds in which $R^2$ is hydrogen and $R^5$ is methyl. Still further preferred as 5α-reductase inhibitors are those compounds in which $R^1$ is —C(O)NR$^3$R$^4$, wherein $R^3$ and $R^4$ are each independently hydrogen or $C_{1-6}$ alkyl. In addition, those compounds wherein $R^1$ is ($C_{1-6}$ alkyl)—OZ$^2$ where $Z^2$ is defined as above and, particularly, where $R^1$ is —CH(CH$_3$)—CH$_2$OZ$^2$, are further useful because, in addition to their activity as inhibitors of 5α-reductase, they also inhibit $C_{17-20}$ lyase.

Acid addition salts of the aforesaid compounds wherein R is hydrogen or $C_{1-6}$ alkyl, with pharmaceutically acceptable acids, are equivalent to the above amines for the purposes of this invention. Illustrative of such salts are the salts with inorganic acids such as, for example, hydrochloric, hydrobromic, sulfuric, phosphoric and like acids; with organic carboxylic acids such as, for example, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, mandelic and like acids; and with organic sulfonic acids such as methanesulfonic acid and p-toluenesulfonic acids.

Examples of compounds of the present invention are the following:

4-Aminopregn-4-ene-3,20-dione.
4-Aminopregna-1,4-diene-3,20-dione.
4-Aminopregna-4,9(11)-diene-3,20-dione.
4-Amino-7-methylpregn-4-ene-3,20-dione.
4-Amino-19-norpregn-4-ene-3,20-dione.
4-Amino-3-oxoandrost-4-ene-17β-carboxamide.
4-Amino-N-(1,1-dimethylethyl)-3-oxoandrosta-4-ene-17β-carboxamide.
4-Amino-N-(1,1-dimethylethyl)-6-methylene-3-oxoandrost4-ene-17β-carboxamide.
4-Amino-N,N-diethyl-3-oxoandrost-4-ene-17β-carboxamide.
4-Amino-N-cyclohexyl-3-oxoandrost-4-ene-17β-carboxamide.
4-Amino-N,N-pentamethylene-3-oxoandrost-4-ene-17β-carboxamide.
2-[4-Amino-N-(1,1-dimethylethyl)-3-oxoandrost-4-en-17β-yl]acetamide.
4-Amino-3-oxopregn-4-ene-20-carboxylic acid.
4-Amino-3-oxopregn-20-carboxylic acid methyl ester.
4-Amino-N,N-diethyl-3-oxopregn-4-ene-20-carboxamide.
4',5'-Dihydrospiro[4-aminoandrosta-4-ene-17,2'(3'H)-furan]-3-one.
4-Amino-N,N-bis(1-methylethyl)-3-oxoandrosta-1,4-diene-17β-carboxamide.
4-Aminopregn-4-ene-3,11,20-trione.
4-Amino-17β-hydroxymethylandrost-4-en-3-one.
4-Amino-20-hydroxypregn-4-en-3-one.
4-Amino-N-(1,1-dimethylethyl)-7-methyl-3-oxoandrost-4-ene-17β-carboxamide.
4-(Methylamino)-N-(1,1-dimethylethyl)-3-oxoandrost-4-ene-17β-carboximide.
(20S)-4-Amino-21-hydroxy-20-methylpregn-4-en-3-one.
(20S)-4-(Methylamino)-21-hydroxy-20-methylpregn-4-en-3-one.
(20S)-4-Amino-21-methoxy-20-methylpregn-4-en-3-one.
(20S)-4-Amino-21-(phenylmethoxy)-20-methylpregn-4-en-3-one The present invention further provides a method for treating a patient afflicted with a DHT-mediated disease or condition which comprises administering to said patient an effective 5α-reductase inhibitory amount of a compound of the present invention. As used herein, the term "patient" refers to a warm-blooded animal, such as a human, which is afflicted with a DHT-mediated disease or condition. DHT-mediated diseases or conditions are those which are associated with elevated androgen activity due to the excessive formation of DIT. Such DHT-mediated diseases or conditions include acne, acne vulgaris, benign prostatic hypertrophy, androgenic alopecia (common baldness caused by androgen in genetically susceptible men and women), seborrhea and female hirsutism. The present invention further relates to the treatment of the particular DHT-mediated diseases and conditions described above.

The present invention further relates to 4-azidosteroids which serve as intermediates to the aminosteroids described earlier. Specifically it also relates to novel 4-azidosteroids which have the following structure:

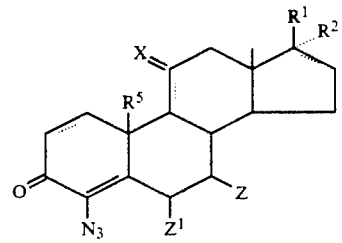

wherein $R^1$, $R^2$, $R^5$, X, Z and $Z^1$ are defined as above with the proviso that $R^1$ is not $C_{2-6}$ alkanoyl. Some of these azido compounds are also useful as 5α-reductase inhibitors.

The 4-amino-4-ene compounds of the present invention are prepared by the reaction of an azido compound of the structure:

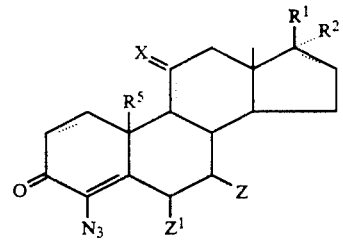

wherein $R^1$, $R^2$, $R^5$, X, Z and $Z^1$ are defined as above, with triphenylphosphine with heating in an aqueous inert solvent. Aqueous tetrahydrofuran is an example of a useful solvent for the reaction. The amino compound obtained in this way can then be reacted with an appropriate anhydride to give the corresponding 4-amide. In the case of the formamido compound, mixed formic acetic anhydride, prepared in situ, is used.

The 4-azidosteroid-4-ene compound used as the starting material above is obtained by reacting the corresponding 4,5-epoxy compound with sodium azide in an inert solvent such as dimethyl sulfoxide in the presence of a catalytic amount of sulfuric acid. The reaction mixture is heated at 60° C. to give the azido compound. The 4,5-epoxy compound is itself obtained by the base catalyzed epoxidation of the corresponding 4-ene using 30% aqueous hydrogen peroxide. For those compounds containing a double bond at the 1-position, it is more convenient to introduce that unsaturation after the epoxide is formed but before it is reacted with sodium azide. Thus, for example, treatment of a 4,5-epoxy 3-ketone with dichlorodicyanoquinone gives the corresponding $\Delta^1$-epoxide compound. The epoxide product obtained is generally a mixture of the $\alpha$- and $\beta$-epoxides with the $\beta$-epoxide being the preponderant product. In some instances, only a single epoxide is formed. In any case, further reaction of the epoxides with sodium azide, as described earlier, gives the desired 4-azidosteroid-4-ene.

The starting materials used in the above syntheses are known compounds and/or they can be prepared by standard known procedures. For example, to obtain compounds in which $Z^1$ is methylene, the appropriate 3-oxo-$\Delta^4$-steroid is reacted with formaldehyde diethyl acetal, phosphorus oxychloride and anhydrous sodium acetate in chloroform, with heating, to give the corresponding 6-methylene-3-oxo-$\Delta^4$-steroid. Treatment of this compound with 30% hydrogen peroxide at 15° C. gives the 4,5-epoxide which is then reacted as described previously.

For those compounds in which $R^5$ is hydrogen, estrone 3-methyl ether can be used as the starting material. The desired substitution at the 17-position is introduced by standard procedures. Birch reduction of the aromatic A-ring followed by acidification gives the corresponding 3-oxo-$\Delta^4$-19-norsteroid which is then converted to the epoxide and reacted further as described earlier. Variations in this procedure and the order in which the reactions are carried out are also possible. Thus, starting with the appropriately substituted steroid, it is possible to carry out a Birch reduction and obtain 20-hydroxy-19-norpregn-4-en-3-one. Treatment of this compound with hydrogen peroxide then gives the corresponding 4,5-epoxide and oxidation of the 20-hydroxy group gives 4,5-epoxy-19-norpregnane-3,20-dione which is then reacted as described earlier.

The steroid 4-enes, which are used as starting materials above, are themselves known compounds or they can be prepared by know standard chemical procedures. The starting materials containing an ether group in the 17-substituent can be prepared from the corresponding alcohol. Thus, for example, a 17-(hydroxyalkyl substituted) steroid-4-en-3-one is first converted to the corresponding 3-methoxysteroid-3,5-diene by reaction with trimethyl orthoformate and a trace of p-toluenesulfonic acid in dioxane as the solvent. Pyridine is used to work up this reaction mixture. Alternatively, the 3-ketone can be protected as the ethylene ketal. In either case the resulting alcohol is then reacted with sodium hydride in dimethylformamide to give the corresponding sodium salt which is then reacted with the appropriate halide, such as methyl iodide or benzyl bromide, to give the corresponding compound containing an ether group as part of the 17-substituent. This ether is then treated with 10% hydrochloric acid, either as part of the general isolation procedure or after isolation of the crude product, to convert the 3-enol ether structure back to the desired steroid-4-en-3-one.

The 4-amino compounds of the present invention in which $R^1$ is -COOH or a similar acid group can be obtained by the alkaline hydrolysis of the corresponding alkyl ester. Those 4-amino compounds in which R is $C_{1-4}$ alkyl are obtained by reaction of an appropriate 4,5-epoxy compound with an appropriate alkylamine.

The foregoing syntheses are illustrative of the preparation of the present compounds and many other conventional reactions and combinations of these reactions may be used to produce or to interconvert the compounds of the invention. These conventional reactions and conditions may be found, e.g., in Fiese, et al., "Steroids" (Reinhold, New York, 1959); Djerassi, Ed., "Steroid Reactions" (Holden-Day, San Francisco, 1963); Kirk et al., "Steroid Reaction Mechanisms" (Elsevier, Amsterdam, 1968); Carruthers, "Some Modern Methods of Organic Synthesis" (Cambridge U. Press, Cambridge, 1971); and Harrison et al., "Compendium of Organic Synthetic Methods" (Wiley-Interscience, New York, 1971).

The compounds of the present invention are useful as 5$\alpha$-reductase inihibitors. Accordingly, they are useful in the treatment of the various diseases and conditions which would be affected by such inhibitors as described above.

The activity of the present compounds as 5$\alpha$-reductase inhibitors can be demonstrated by the following standard test procedure Microsomal preparations of the steroid 5$\alpha$-reductase enzyme (protein) were obtained from human prostate tissue and stored in aliquots. Protein concentration was determined prior to use of the samples. In the method itself, individual assays for 5$\alpha$-reductase activity contained 0.1M phosphate citrate buffer, pH 5.6, 1 mM EDTA, 7 to 22 $\mu$g of microsomal protein, 1 mM NADPH, 5 mM glucose-6-phosphate, 1 IU/ml glucose-6-phosphate dehydrogenase, 1,2-$^3$H-testosterone, and test compound, dissolved in dimethyl sulfoxide and then diluted in phosphate-citrate buffer to yield a final assay concentration of 0.1% (v/v) dimethyl sulfoxide. The same buffer and the same quantity of dimethyl sulfoxide, without any test compound was used for the control assays. The total assay volume was 100 $\mu$l and assays were performed in duplicate. The reaction was initiated by the addition of the testosterone, and incubated for 30 minutes at 25° C. The assay is linear with time to 30 minutes.

Depending on the nature of the inhibition, testosterone concentration was typically varied from 0.15 $\mu$M (approximately 0.5 K$_m$) to 10 K$_m$ with radioactive label constant at 0.15 $\mu$Ci per assay. The amount of test compound added was varied to provide final concentrations of 1 nM to 100 $\mu$M. The reaction was quenched by the addition of 50 volumes of chloroform:methanol (2:1). The steroids were then extracted and separated by high pressure liquid chromatography and the amounts of testosterone and dihydrotestosterone present were measured to determine the percent conversion of testosterone to dihydrotestosterone and to calculate the 5$\alpha$-reductase activity. The activity of the test compound was then expressed as the IC$_{50}$, or the concentration of test compound that produced a 50% inhibition of the testosterone conversion. When compounds of the present invention were tested in this way, the following results were observed:

| Test Compound | IC$_{50}$(nM) |
| --- | --- |
| 4-Aminopregn-4-ene-3,20-dione | 50 |
| N,N-Diisopropyl-4-amino-3-oxoandrost-4-ene-17$\beta$-carboxamide | 104 |
| N-(t-Butyl)-4-amino-3-oxoandrost-4-ene-17$\beta$-carboxamide | 59 |
| (20S)-4-Amino-21-hydroxy-20-methyl- | 54 |

| Test Compound | IC$_{50}$(nM) |
| --- | --- |
| pregn-4-en-3-one | |

To achieve the desired anti-acne or anti-seborrheic effect the compounds employed in the present invention can be administered orally, parenterally, for example, intramuscularly and subcutaneously, and topically to a patient in need of treatment. Topical administration is preferred. As used herein in association with the treatment of acne or oily skin, the term patient is taken to mean a warm-blooded mammal, for example, primates, human males and females having an acne condition or an oily skin condition in need of treatment. The compounds of the invention can be administered alone or suitably admixed in the form of a pharmaceutical preparation to the patient being treated. The amount of compound administered will vary with the severity of the acne condition or oily skin condition and repetitive treatment may be desired. For oral and parenteral administration, the amount of compound administered, that is, the anti-acne or anti-seborrheic effective amount, is from 0.001 to 10 mg/kg of body weight per day and preferably from 0.01 to 1.0 mg/kg of body weight per day. Unit dosages for oral or parenteral administration may contain, for example, from 0.2 to 100 mg of the active ingredient. For topical administration the anti-acne or anti-seborrheic effective amount of the compounds of the invention on a percent basis can vary from 0.001% to 5% and preferably from 0.005% to 1%. For topical administration the formulated active ingredient, that is, a compound of the invention can be applied directly to the site requiring treatment or can be applied to the oral or nasal mucosa. Applicator sticks carrying the formulation may be employed in administering the compounds.

In the treatment of benign prostatic hypertrophy (BPH) the compounds of the invention may be administered in various manners to the patient being treated to achieve the desired effect. As used herein in the treatment of BPH, the term patient is taken to mean male warm blooded animals, such as male dogs and human males. The compounds can be administered alone or in combination with one another. Also, the compounds can be administered in the form of a pharmaceutical preparation. The compounds may be administered orally, parenterally, for example, intravenously, intraperitoneally, intramuscularly or subcutaneously, including injection of the active ingredient directly into the prostate. Slow release implants can also be used. The amount of compound administered will vary over a wide range and can be any effective amount. Depending on the patient to be treated, the condition being treated and the mode of administration, the effective amount of compound administered will vary from about 0.001 to 10 mg/kg of body weight per day and preferably from 0.01 to 1.0 mg/kg of body weight per day. Unit dosages for oral or parenteral administration may contain, for example, from 0.2 to 100 mg of a compound of the invention.

These dosage ranges represent the amount of compound that will be effective in reducing the size of the prostate, i.e., the amount of compound effective in treating BPH. The compounds can be administered from onset of hypertrophy of the prostate to regression of the symptoms, and may be used as a preventive measure.

The compounds of the present invention may be administered either as individual therapeutic agents or as mixtures with other therapeutic agents. They may be administered alone but are generally administered in the form of pharmaceutical compositions, i.e., mixtures of the active agents with suitable pharmaceutical carriers or diluents. Examples of such compositions include tablets, lozenges, capsules, powders, aerosol sprays, aqueous or oily suspensions, syrups, elixirs and aqueous solutions for injection. The compounds are most preferably administered in oral dosage forms.

The nature of the pharmaceutical composition and the pharmaceutical carrier or diluent will, of course, depend on the desired route of administration, i.e., orally or parenterally. Oral compositions may be in the form of tablets or capsules and may contain conventional excipients such as binding agents (e.g., syrup, acacia, gelatin, sorbitol, tragacanth or polyvinylpyrrolidone), fillers (e.g., lactose, sugar, maize-starch, calcium phosphate, sorbitol or glycine), lubricants (e.g., magnesium stearate, talc, polyethylene glycol or silica), disintegrants (e.g., starch) or wetting agents (e.g., sodium lauryl sulfate). Oral liquid preparations may be in the form of aqueous or oily suspensions, solutions, emulsions, syrups, elixirs, etc., or may be presented as a dry product for reconstitution with water or other suitable vehicle before use. Such liquid preparations may contain conventional additives such as suspending agents, flavoring agents, diluents or emulsifying agents. For parenteral administration, solutions or suspensions of a compound of the present invention with conventional pharmaceutical vehicles may be employed, e.g., as an aqueous solution for intravenous injection or as an oily suspension for intramuscular injection. Procedures for the preparation of compositions as discussed above are described in standard texts, such as *Remington's Pharmaceutical Sciences*, Mack Publishing Company, Easton, Pa.

The following are illustrative pharmaceutical formulations suitable for oral administration which may be employed in practicing the present invention:

| TABLET | |
| --- | --- |
| (a) N-(t-Butyl)-4-amino-3-oxoandrost-4-ene-17β-carboxamide | 75 g |
| (b) Lactose | 1.216 Kg |
| (c) Corn starch | 0.3 Kg |

Mix the active ingredient, the lactose and corn starch uniformly. Granulate with 10% starch paste. Dry to a moisture content of about 2.5%. Screen through a No. 12 mesh screen. Add and mix the following:

| | |
| --- | --- |
| (a) Magnesium stearate | 0.015 Kg |
| (b) Corn starch qs ad | 1.725 Kg |

Compress on a suitable tablet machine to a weight of 0.115 g/tablet.

| SOFT GELATIN CAPSULE | |
| --- | --- |
| (a) N-(t-Butyl)-4-amino-3-oxoandrost-4-ene-17β-carboxamide | 0.25 Kg |
| (b) Polysorbate 80 | 0.25 Kg |
| (c) Corn oil qs ad | 25.0 Kg |

Mix and fill into 50,000 soft gelatin capsules.

The following examples are presented to illustrate the present invention but they should not be construed as limiting it in any way.

EXAMPLE 1

N-(1,1-Dimethylethyl)-4,5-epoxy-3-oxoandrostane-17β-carboxamide

A solution of N-(1,1-dimethylethyl)-3-oxoandrost-4-ene-17β-carboxamide (4.77 g, 12.8 mmole) in methanol (55 mL) and dichloromethane (11 mL) was cooled to 12° C. and treated in one portion with 30% aqueous hydrogen peroxide (3.3 mL) followed by dropwise addition of an aqueous sodium hydroxide solution prepared by dissolving sodium hydroxide (0.38 g) in water (2.2 mL). After one hour, the cooling bath was removed and the reaction was stirred for an additional 3 hours. Most of the solvent was then removed in vacuo. The residue was dissolved in dichloromethane and purified by flash chromatography (hexane-20% ethyl acetate and hexane40% ethyl acetate) to give N-(1,1-Dimethylethyl)-4,5-epoxy-3-oxoandrostane-17β-carboxamide (3.3 g, 66.2%) as a solid foam. This material was a mixture of the 4α,5α- and 4β,5β-isomers and it was used as is in further reactions.

EXAMPLE 1A

When the procedure of Example 1 was repeated using the appropriate starting materials, the following compounds were obtained, usually as a mixture of the two isomeric epoxides:

N,N-Bis(1-methylethyl)-4,5-epoxy-3-oxoandrostane-17β-carboxamide (73.5%).

(20S)-4,5-Epoxy-3-oxopregnane-20-carboxylic acid methyl ester (61.3%).

4,5-Epoxypregnane-3,20-dione (87.6%).

4,5-Epoxy-17α-hydroxypregnane-3,20-dione (79.1%).

4,5-Epoxypregnane-3,11,20-trione (41.8%).

(20S)-4,5-Epoxy-21-hydroxy-20-methylpregnan-3-one (73.1%).

(20S)-4,5-Epoxy-21-methoxy-20-methylpregnan-3-one (64%).

4,5-Epoxy-20-hydroxypregnan-3-one (46.0%).

4,5-Epoxypregn-9(11)-ene-3,20-dione (75.5%).

EXAMPLE 2

N-(1,1-Dimethylethyl)-4-azido-3-oxoandrost-4-ene-17β-carboxamide

A solution of N-(1,1-Dimethylethyl)-4,5-epoxy-3-oxoandrost-4-ene-17β-carboxamide (3.6 g, 9.29 mmole) in dimethyl sulfoxide (50 mL), under a nitrogen atmosphere, was placed into an oil bath heated to 60° C. The solution was stirred vigorously as sodium azide (9.74 g, 149.8 mmole) was slowly added. Concentrated sulfuric acid (0.6 mL) was then added dropwise and the mixture was stirred at 60° C. for 90 minutes. The reaction flask was removed from the oil bath and cooled to room temperature. The resulting solid mass was broken up and poured into ice-cold water (500 mL). The mixture was stirred for 30-45 minutes after which the solids were collected by filtration, washed with water and sucked dry to give crude azide. The azide was taken up in dichloromethane and purified by flash chromatography through a column of silica gel eluting with hexane-15% ethyl acetate and hexane30% ethyl acetate. Fractions containing the desired product were combined and concentrated in vacuo to give N-(1,1-dimethylethyl)-4-azido-3-oxoandrost-4-ene-17β-carboxamide as a white solid (1.7 g, 44.4%) which was crystallized from diethyl ether-hexane. IR 3422, 2114, 1672, 1592(w) cm$^{-1}$; MS (CI) m/z 413 (40%, M$^+$+1), 385 (100%, M$^+$+1−N$_2$), (EI) m/z 413 (4%, M$^+$+1), 58 (100%); $^1$H NMR (CDCl$_3$) δ 0.71 (3H, s, C$_{18}$-Me), 1.18 (s, C$_{19}$-Me), 1.35 (s, 'Bu-Me's), 3.03 (1H, dq, C$_6$β-H), 5.08 ppm (1H, s, NH); $^{13}$C NMR (downfield signals only) (CDCl$_3$) δ 128.53, 154.84, 171.58, 193.14 ppm. This compound has the following structure:

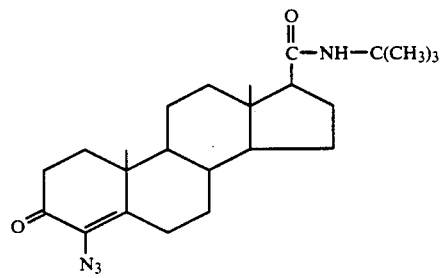

EXAMPLE 2A

When the procedure of Example 2 was repeated using the appropriate starting materials the following compounds were obtained:

4-Azido-N,N-bis(1-methylethyl)-3-oxoandrost-4-ene-17β-carboxamide, IR 3435, 2110, 1680, 1635, 1595(w) cm$^{-1}$; MS (CI) m/z 441 (15%, M$^+$+1), 413 (100%); (EI) m/z 412 (5%, M$^+$−N$_2$), 86 (100%); $^1$H NMR (CDCl$_3$) δ 0.78 (3H, s, C$_{18}$-Me), 1.12 (d, ½ $^i$PrMe), 1.18+1.21 (s+d, C$_{19}$-Me+½ $^i$PrMe), 1.39 +1.41 (pr d, $^i$PrMe), 2.98–3.08 (1H, pr m), 3.40 (1H, hept, prCH); $^{13}$C NMR 128.49, 154.99, 171.73, 193.18.

(20S)-4-Azido-3-oxopregn-4-ene-20-carboxylic acid methyl ester, (contains starting epoxide as an impurity) IR 2110, 1736, 1676 cm$^{-1}$; MS (CI) m/z 400 (30%, M$^+$+1), 372 (100%); (EI) m/z 400 (2%, M$^+$+1), 399 (1%, M), 256 (100%); $^1$H NMR (CDCl$_3$) δ 0.58+0.59 (pr s, 2×C$_{18}$-Me), 1.15+1.17 (pr s, 2×C$_{19}$-Me), 1.18 (d, C$_{21}$-Me), 2.97+3.10 (s+pr q, C$_4$-H+C$_{6α}$-H), 3.64 (s, CH$_3$O); $^{13}$C NMR (CDCl$_3$) δ 128.47, 155.03, 177.08, 177.11, 193.17, 206.69.

4-Azidopregn-4-ene-3,20-dione, IR 2115, 1710, 1670, 1590; MS (CI) m/z 356 (20%, M$^+$+1), 328 (100%); (EI) m/z 355 (1%, M$^+$) 43 (72%); $^1$H NMR (CDCl$_3$) δ 0.67 (3H, s, C$_{18}$-Me), 1.19 (s, C$_{19}$-Me), 2.12 (3H, s, C$_{21}$-Me), 2.42–2.62 (3H, m), 3.20 (1H, dq); $^{13}$C NMR (CDCl$_3$) δ 128.52, 154.71, 193.15, 209.26.

4-Azido-17α-hydroxypregn-4-ene-3,20-dione, IR 3495, 2112, 1702, 1678sh, 1658 cm$^{-1}$; MS (CI) m/z 372 (10%, M$^+$+1) 344 (100%); (EI) m/z 371 (1%, M$^+$), 43 (100%); $^1$H NMR (CDCl$_3$) δ 0.78 (3H, s, C$_{18}$-Me), 1.18 (3H, s, C$_{19}$ -Me), 2.26 (3H, s, C$_{21}$-Me); $^{13}$C NMR (CDCl$_3$) δ 89.70, 128.57, 154.68, 193.14, 211.50.

4-Azidopregn-4-ene-3,11,20-trione, Anal. Calcd for C$_{21}$H$_{27}$N$_3$O$_3$: C, 68.27; H, 7.37; N,11.37; Found: C, 67.67; H, 7.68; N, 8.14. IR 3484, 2112, 1726, 1698, 1666 cm$^{-1}$; MS (CI) 388 (40%, M$^+$+1), 360 (100%); (EI) 359 (0.8%), 43 (100%); $^1$H NMR (DMSO-D$_6$) δ 0.45+0.51 (3H, pr s 4:1, C$_{18}$ -Me), 1.27+1.33 (pr s 4:1), 2.04+2.06 (pr s), 4.26 (1H, s), 5.06 (1H, s); $^{13}$C NMR (DMSO-D$_6$) δ 205.38, 208.04, 210.48.

(20S)-4-Azido-21-hydroxy-20-methylpregn-4-en-3-one, IR 3408, 2112, 1676 cm$^{-1}$; MS (CI) m/z 372 (5%, M$^+$+1), 344 (100%, M+1-N$_2$; (EI) m/z 371 (3%, M), 55 (100%); $^1$H NMR (CDCl$_3$) δ 0.70 (3H, s C$_{18}$-

Me), 1.04 (d, $C_{21}$-Me), 1.18 (S, $C_{19}$-Me), 2.41 –2.60 (2H, m), 3.20 (1H, dq, $C_6$-H), 3.38 (1H, dd, ½ $C_{21}$-CH$_2$), 3.63 (1H, dd, ½ $C_{21}$-CH$_2$); $^{13}$C NMR (CDCl$_3$) δ 128.39, 155.34, 193.26.

4-Azidopregna-4,9(11)-diene-3,20-dione, IR 2118, 1706, 1668, 1638 cm$^{-1}$; MS (CI) m/z 354 (20%, M$^+$+1), 326 (100%, M$^+$+1−N$_2$); (EI)m/a 353(0.1%, M+), 43(100%).

4-Azido-20-hydroxypregn-4-en-3-one, IR 3560, 2114, 1670, 1592 cm$^{-1}$; MS (CI) m/z 358 (15%, M$^+$+1), 330 (100% M$^+$+1 -N$_2$); $^1$H NMR (CDCl$_3$) δ 0.71 (minor)+0.78 (3H, s+s, $C_{18}$-Me's, 1:19); 1.14 (d, $C_{22}$-Me), 1.18 (s, $C_{19}$-Me), 3.02 (1H, dq, $C_{6\alpha}$-H), 3.67–3.78 (1H, m, $C_{20}$-H); $^{13}$C NMR (CDCl$_3$) δ$^{major}$ 128.41, 155.34, 193.29.

(20S)-4-Azido-21-hydroxy-20-methylpregn-4-en-3-one benzoate, IR 3436, 2112, 1710, 1676, 1594, 1274 cm$^{-1}$; MS (CI) m/z 476 (10%, M$^+$+1), 326 (100%, M$^+$+1 -N$_2$- PhCO$_2$H); $^1$H NMR (CDCl$_3$) δ 0.76 (3H, s, $C_{18}$-Me), 1.12 (d, $C_{20}$-Me), 1.18 (s, $C_{19}$-Me), 3.02 (1H, dq, $C_{6\alpha}$-H), 4.04 (1H, dd, ½ $C_{21}$-CH$_2$), 4.32 (1H, dd, ½ $C_{21}$-CH$_2$), 7.45 (2H, t), 7.52–7.60 (1H, m), 8.04 (2H, dd); $^{13}$C NMR (CDCl$_3$) δ 128.31, 128.42, 129.46, 130.47, 132.80, 155.22, 166.66, 193.22.

(20S)-4-Azido-21-methoxy-20-methylpregn-4-en-3-one, IR 3437, 2108, 1673, 1634(m) cm$^{-1}$; MS (CI) m/z 386 (25% M$^+$+1), 358 (100%, M$^+$+1 -N$_2$); $^1$H NMR δ 0.71 (3H, s, $C_{18}$-Me), 1.02 (d, $C_{20}$-Me), 1.17 (s, $C_{19}$-Me), 2.40–2.60 (2H, m), 3.01 (1H, dq, $C_{6\alpha}$-H), 3.10 (1H, dd, ½ $C_{21}$-CHhd 2), 3.31+3.32 (4H, s+dd, MeO+½ $C_{21}$-CH$_2$); $^{13}$C NMR δ 78.08, 128.44, 155.40, 193.29.

EXAMPLE 3

4-Amino-N-(1,1-dimethylethyl)-3-oxoandrost-4-ene-17β-carboxamide

To a stirred solution of N-(1,1-dimethylethyl)-4-azido-3-oxoandrost-4-ene-17β-carboxamide (1.3 g, 3.15 mmole) in tetrahydrofuran (20mL)-water (7 mL) was added triphenylphosphine (1.41 g, 5.38 mmole). The reaction was heated at reflux temperature for 16 hours. Most of the tetrahydrofuran was removed under vacuum. Dichloromethane was added to the mixture and the organic solution was placed atop a column of silica gel and flash chromatographed (hexane-30% ethyl acetate). The fractions containing the product were combined and concentrated to a white solid which was crystallized from diethyl ether to give the 4-amino-N-(1,1-dimethylethyl)-3-oxoandrost-4-ene-178-carboxamide (0.67 g, 54.9%). IR 3476, 3442, 3382, 1672, 1659, 1620(m), 1580(m) cm$^{-1}$; MS (CI) m/z 387 (100%, M$^+$+1); (EI) m/z 386 (10%, M$^+$), 343 (100%); $^1$H NMR (CDCl$_3$) δ 0.72 (3H, s, $C_{18}$-Me), 1.16 (s, $C_{19}$-Me), 1.34 (s, $^t$Bu-Me's), 3.49 (2H, br s, NH$_2$), 5.08 (1H, s, NHCO); $^{13}$C NMR (CDCl$_3$) δ 132.97, 138.39, 171.69, 194.22. This compound has the following structure:

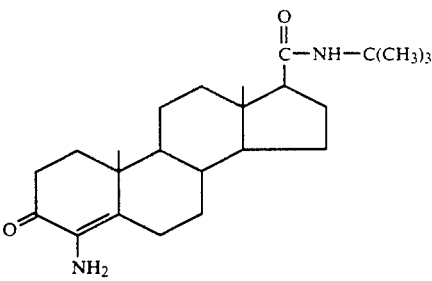

EXAMPLE 3A

When the procedure of Example 3 was repeated using the appropriate starting materials, the following compounds were obtained:

4-Amino-N,N-bis(1-methylethyl)-3-oxoandrost-4-ene-17β-carboxamide, IR 1668, 1634 cm$^{-1}$; MS (CI) m/z 415 (100%, M$^+$+1); (EI) m/z 414 (95%, M$^+$), 371 (100%); $^1$H NMR (CDCl$_3$) 0.80 (s, $C_{18}$-Me), 1.12+1.21 (pr d, 2×$^i$Pr-Me), 1.15 (s, $C_{19}$-Me), 1.38+1.41 (pr d, 2×$^i$Pr-Me), 2.8–3.3 (2H, br, NH$_2$), 3.38 (1H, hept, $^i$PrCH), 4.19 (1H, hept, $^i$PrCH); $^{13}$C NMR (CDCl$_3$) δ 121.83, 132.16, 132.64, 136.23, 171.63, 194.29.

(20S)-4-Amino-3-oxopregn-4-ene-20-carboxylic acid methyl ester, IR 3464, 3370, 1728, 1666, 1624, 1586, 1172 cm$^1$; MS (CI) m/z 374 (100%, M$^+$+1); (EI) m/z 373 (70%, M$^+$), 330 (100%); $^1$H NMR (CDCl$_3$) δ 0.73 (3H, s, $C_{18}$-Me), 1.16 (s, $C_{19}$-Me), 1.19 (d, $C_{21}$-Me), 3.45 (2H, br, NH$_2$), 3.65 (3H, s, CH$_3$O); $^{13}$C NMR (CDCl$_3$) δ 132.93, 138.66, 177.19, 194.27.

4-Aminopregn-4-ene-3,20-dione, IR 3460, 3360, 1700, 1670, 1615, 1580 cm$^{-1}$; MS (CI) m/z 330 (100%, M$^+$+1); (EI) m/z 329 (40%, M$^+$), 286 (100%); $^1$H NMR (CDCl$_3$) δ0.67 (3H, s, $C_{18}$-Me), 1.15 (s, $C_{19}$-Me), 2.12 (s, $C_{21}$-Me), 3.47 (2H, br s, NH$_2$); $^{13}$C NMR 132.95, 138.12, 194.11, 209.22.

4-Amino-17α-hydroxypregn-4-ene-3,20-dione, IR 3462, 3362, 1704, 1654, 1618, 1588 cm$^{-1}$; MS (CI) m/z 346 (100%, M$^+$+1); (EI) m/z 345 (45%, M$^+$), 32 (100%); $^1$H NMR (CDCl$_3$) δ 0.76 (3H, s, $C_{18}$-Me), 1.15 (3H, s, $C_{19}$-Me), 2.28 (3H, s, $C_{21}$-Me), 3.3–3.6 (2H, br s, NH$_2$); $^{13}$C NMR (CDCl$_3$) δ 89.85, 133.05, 138.23, 194.23, 211.59.

(20S)-4-Amino-21-hydroxy-20-methylpregn-4-en-3-one, IR 3510, 3470, 3384, 1648, 1614, 1576 cm$^{-1}$; MS (CI) 346 (100%, M$^+$+1) (EI) 345 (65%, M$^+$), 302 (100%); $^1$H NMR δ (CDCl$_3$) 0.73 (3H, s, $C_{18}$-Me), 1.04 (d, $C_{21}$-Me), 1.15 (s, $C_{19}$-Me), 2.42–2.56 (3H, m), 3.73 (v br, NH$_2$) 3.36 (1H, dd, ½ $C_{21}$-CH$_2$), 3.63 (1H, dd, ½ $C_{21}$-CH$_2$); $^{13}$C NMR δ (CDCl$_3$) 132.85, 139.15, 194.38.

1-Aminopregn-4-ene-3,11,20-trione, IR 3450, 3354, 1702, 1668, 1614, 1758cm$^{-1}$; MS(CI) m/z 344 (100%, M$^+$+1) (EI) m/z 343 (95%, M$^+$), 328 (100%); $^1$H NMR (CDCl$_3$) δ 0.63 (3H, s, $C_{18}$-Me), 1.48 (s, $C_{19}$-Me), 2.11 (s, $C_{21}$-Me), 3.50 (2H, s, NH$_2$); $^{13}$C NMR (CDCl$_3$) δ 133.53, 135.50, 194.59, 207.83, 208.72.

4-Amino-20-hydroxypregn-4-en-3-one, IR 3410, 1670, 1622, 1586 cm$^{-1}$; MS (CI) m/z 332 (100%, M$^+$+1), 314 (30%, M$^+$+1-H$_2$O); $^1$H NMR (CDCl$_3$) δ 0.78 (major)+0.82, (s+s, $C_{18}$-Me'S), 1.14 (s, ½ $C_{21}$-Me), 1.16 (s, $C_{19}$-Me), 3.00 (2H, v br, NH$_2$), 3.67–3.79 (1H, m, $C_{20}$-H).

(20S)-4-Amino-21-hydroxy-20methylpregn-4-en-3-one 21-benzoate, IR 3448, 3361, 1720, 1665, 1618, 1602, 1582, 1278 cm$^{-1}$ MS (CI) m/z 450 (90%, M++1), 328 (100%, M++1-PhCO$_2$H); $^1$H NMR (CDCl$_3$) δ 0.77 (3H, s, C$_{18}$-Me), 1.12 (d, C$_{22}$-Me), 1.14 (s, C$_{19}$-Me), 3.38 (2H, v br, NH$_2$), 4.05 (1H dd, ½ C$_{21}$-CH$_2$), 4.32 (1H, dd, ½ C$_{21}$-CH$_2$), 7.40–7.47 (2H, m), 7.53–7.59 (1H, m), 8.01–8.07 (2H, m); $^{13}$C NMR (CDCl$_3$) δ 128.32, 129.48, 130.51, 132.80, 132.89, 138.89, 166.71, 194.31.

(20S)-4-Amino-21-methoxy-20-methylpregn-4-en-3-one, IR 3478, 3361, 1675, 1620, 1580 cm$^{-1}$.

EXAMPLE 4

4-Acetamido-N-(1,1-dimethylethyl)-3-oxoandrost-4-ene-17β-carboxamide

A solution of 4-amino-N-(1,1-dimethylethyl)-3-oxoandrost-4-ene-17β-carboxamide (0.9 g, 2.34 mmole) in acetic anhydride (3mL) and pyridine (6 mL) is stirred overnight at room temperature. Water is added and the mixture is stirred for 3 hours. The solids are collected by filtration to give a brown solid which is purified by flash chromatography (hexane-50% ethyl acetate then ethyl acetate) to give 4-acetamido-N-(1,1-dimethylethyl)-3-oxoandrost-4-ene-17β-carboxamide. This compound has the following structure:

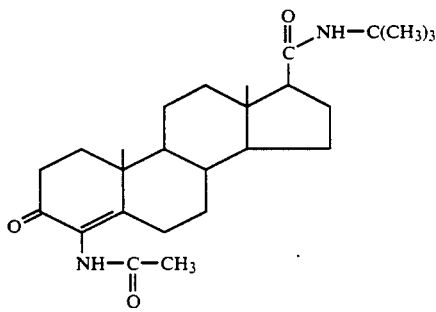

EXAMPLE 4A

When the procedure of Example 4 is repeated using the appropriate starting materials, the following compounds are obtained:
4-Acetamidopregn-4-ene-3,20-dione.
4-Acetamido-N,N-bis(1-methylethyl)-3-oxoandrost-4-ene-17β-carboxamide.
(20S)-4-Acetamido-21-hydroxy-20-methylpregn-4-en-3-one-acetate.

EXAMPLE 5

4-Formamido-N-(1,1-dimethylethyl)-3-oxoandrost-4-ene-17β-carboxamide

A solution of formic acid (0.22 mL, 5.84 mmole) and acetic anhydride (0.46 mL, 4.76 mmole) is heated at reflux temperature for 2 hours under a nitrogen atmosphere. The cooled solution is diluted with tetrahydrofuran (5 mL) and a solution of 4-amino-N-(1,1-dimethylethyl)-3-oxoandrost-4-ene-17β-carboxamide, (0.35 g, 0.91 mmole) in tetra-hydrofuran (10 mL) is added. The reaction is stirred overnight at room temperature and then diluted with water (25 mL). A gummy material separated which is extracted into diethyl ether-dichloromethane and washed with saturated aqueous sodium bicarbonate. The dried solution is concentrated to a yellow foam which is purified by flash chromatography (hexane-50% ethyl acetate then ethyl acetate) to give 4-formamido-N-(1,1-dimethylethyl)-3-oxoandrost-4-ene-17β-carboxamide (0.25 g, 67.6%, diethyl ether).

EXAMPLE 5A

When the procedure of Example 5 is repeated using the appropriate starting materials, the following compounds are obtained:
4-Formamidopregn-4-ene-3,20-dione.
4-Formamido-N,N-bis(1-methylethyl)-3-oxoandrost-4-ene-17β-carboxamide.

EXAMPLE 6

(20S)-4-Amino-N,N-diethyl-3-oxopregn-4-ene-20-carboxamide

A stirred suspension of 3-oxopregn-4-ene-20-carboxylic acid (2.0 g, 5.8 mmole) in benzene (40 mL) was mixed with pyridine (0.59 mL, 7.3 mmole), cooled in an ice-water bath and treated with oxalyl chloride (0.65 mL, 7.5 mmole). The cooling bath was removed and the reaction mixture was stirred for one hour at room temperature. The mixture was then cooled in an ice-water bath and treated with diethylamine (3.48 mL, 33.7 mmole). After 45 minutes, the reaction was diluted with methylene chloride (100 mL) and extracted with 7% hydrochloric acid (100 mL). The organic layer was separated, dried over magnesium sulfate, treated with charcoal and filtered. The solvent was then removed to leave a white solid which was redissolved in methylene chloride and purified by flash chromatography (ethyl acetate-50% hexane). The resulting solid was recrystallized from aqueous methanol to give (20S)-N,N-diethyl-3-oxopregn-4-ene-20-carboxamide melting at 198°14 199° C.

When the product obtained by the above reaction is reacted with 30% aqueous hydrogen peroxide according to the procedure described in Example 1, the corresponding 4,5-epoxide is obtained. This epoxide is then reacted with sodium azide according to the procedure described in Example 2 to give the corresponding 4-azide which is then reacted with triphenylphosphine according to the procedure described in Example 3 to give (20S)-4-amino-N,N-diethyl-3-oxopregn-4-ene-20-carboxamide.

EXAMPLE 7

(20S)-4-Amino-N-(1,1-dimethylethyl)-3-oxopregn-4-ene-20-carboxamide

A stirred suspension of 3-oxopregn-4-ene-20-carboxylic acid (1.7 g, 5.0 mmole) in benzene (35 mL) was mixed with pyridine (0.56 mL, 6.25 mmole), cooled in an ice-water bath and treated with oxalyl chloride (0.56 mL, 6.45 mmole). The cooling bath was removed and the reaction mixture was stirred for 1.5 hours. The resulting mixture was then cooled in ice and treated slowly with tert-butylamine (2.9 mL, 29 mmole). After thirty minutes, the mixture was diluted with methylene chloride (100 mL), extracted with 5% hydrochloric acid, dried over magnesium sulfate, treated with charcoal, and filtered. The resulting filtrate was concentrated to give a yellow solid which was dissolved in methylene chloride and purified by flash chromatography (hexane-40% ethyl acetate). The product obtained in this way was subjected to flash chromatography again (hexane-30% ethyl acetate) and the resulting product was recrystallized from acetone to give N-(1,1-dimethylethyl)-3-oxopregn-4-ene-20-carboxamide. IR 3445, 3375, 1670 cm$^{-1}$.

When the product obtained by the above reaction is reacted with 30% aqueous hydrogen peroxide according to the procedure described in Example 1, the corresponding 4,5-epoxide is obtained. This epoxide is then reacted with sodium azide according to the procedure described in Example 2 to give the corresponding 4-azide which is then reacted with triphenylphosphine according to the procedure described in Example 3 to give (20S)-4-amino-N-(1,1-dimethylethyl)-3-oxopregn-4-ene-20-carboxamide.

EXAMPLE 8

(20S)-4-Amino-21-hydroxy-20-methylpregn-4-en-3-one

To a stirred solution of (20S)-21-hydroxy-20-methylpregn-4-en-3-one (15.0 g, 45.38 mmol), acetic anhydride (8.6 mL, 90.76 mmol) and triethylamine (9.5 mL, 68.07 mmol) in methylene chloride (25 mL) was added 4-dimethylaminopyridine (277 mg, 277 mmol). After 3 hours at room temperature, the reaction mixture was cooled in an ice-water bath and methanol (4 mL) was added. After 15 minutes, the reaction was diluted with methylene chloride and washed successively with 0.5 N hydrochloric acid, saturated aqueous sodium bicarbonate, water and then brine. The resulting solution was dried over magnesium sulfate and concentrated to give a yellow solid which was recrystallized from a mixture of ether and hexane. This gave (20S)-21-hydroxy-20-methylpregn-4-en-3-one acetate as a white solid (13.75 g, 81%).

To a stirred solution of (20S)-21-hydroxy-20-methylpregn-4-en-3-one acetate (10.2 g, 27.38 mmol) in pyridine (100 mL) cooled to 15° C. there was added sulfuryl chloride (4.4 mL, 54.76 mmol) dropwise. After 30 minutes, the reaction mixture was poured into 1N hydrochloric acid and extracted with ether. The combined organic extracts were successively washed with 1N hydrochloric acid, water, saturated aqueous sodium bicarbonate and brine. The solution was then dried over magnesium sulfate and concentrated to give an orange solid. Flash chromatography of this material [eluting with ethyl acetate-hexane (3:7)]gave (20S)-4-chloro-21-hydroxy-20-methylpregn-4-en-3-one acetate as a white solid (8.5 g, 72%).

Ammonia (about 8 mL) was condensed into a Carius tube which contained (20S)-4-chloro-21-hydroxy-20-methylpregn-4-en-3-one acetate (1.5 g, 3.69 mmol) and which was cooled to −78° C. The tube was sealed, heated to 70° C. for one hour, and then allowed to stand at room temperature overnight. The contents of the tube were poured into a mixture of ether and water and the two layers were separated. The organic layer was extracted with 0.5N hydrochloric acid and the resulting acidic, aqueous solution was washed with ether and then made alkaline with 1N aqueous sodium hydroxide. The resulting alkaline, aqueous mixture was extracted with ether and the ether extracts were dried over magnesium sulfate and concentrated to a yellow, foamy solid. This residue was dissolved in methanol (25 mL) and 2N hydrochloric acid (2 mL) and the resulting mixture was heated to reflux for 15 minutes and then allowed to cool to room temperature. The mixture was extracted with ether, then made alkaline with solid sodium carbonate, and extracted with ether. The organic extracts of the alkaline, aqueous solution were dried over magnesium sulfate and concentrated to give (20S)-4-amino-21-hydroxy-20-methylpregn-4-en-3-one as an off-white solid (50 mg, 4%). This compound has the following structure:

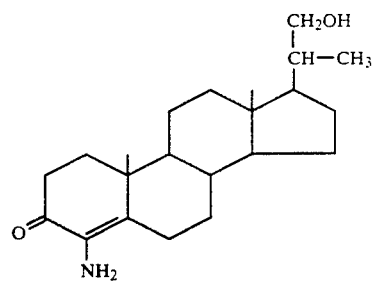

To obtain the corresponding 4-methylamino compound, a suspension of (20S)-4-chloro-21-hydroxy-20-methylpregn-4-en-3-one acetate in methanol was mixed with 40% aqueous methylamine and refluxed for 30 minutes. Additional 40% aqueous methylamine was added and refluxing was continued for another 30 minutes. The solvent was then evaporated and the residue was purified as described above for the 4-amino compound to give (20S)-4-(methylamino)-21-hydroxy-20-methylpregn-4-en-3-one.

EXAMPLE 9

(20S)-4,5-Epoxy-21-hydroxy-20-methylpreqnan-3-one Acetate

To a solution of (20S)-21-hydroxy-20-methylpregn-4-en-3-one acetate (10.6 g, 28.3 mmole) in methanol (60 mL) and dichloromethane (15 mL) cooled to 15° C. in a cold water bath there was added 30% hydrogen peroxide (6.8 mL) and then, dropwise, a solution of sodium hydroxide (0.49 g) in water (3.2 mL). After 30 minutes, the cold bath was removed and the reaction was stirred for 4 hours at room temperature. The solvents were then removed under reduced pressure and the residue was dissolved in dichloromethane (300 mL) and extracted with brine (100 mL). The organic layer was separated, dried over magnesium sulfate, filtered and concentrated to a solid which was purified by flash chromatography on silica gel to give (20S)-4,5-epoxy-21-hydroxy-20-methylpregnan-3-one acetate (6.1 g, 55.6%) as a mixture of the 4α,5α- and 4β,5β-isomers.

EXAMPLE 10

(20S)-4-Azido-21-hydroxy-20-methylpregn-4-en-3-one Acetate

To a vigorously stirred solution of the (20S)-4,5-epoxy21-hydroxy-20-methylpregnan-3-one acetate (3.0 g, 7.72 mmole) obtained in the preceding example, in dimethyl sulfoxide (100 mL), there was added sodium azide (8.2 g) and then concentrated sulfuric acid (0.55 mL). The mixture was heated at 60° C. for 1.5 hours and the cooled mixture was poured into cold water (700 mL). After stirring for 30 minutes, the solids were collected by filtration, washed with water and dried by suction. The resulting solid was purified by flash chromatography on silica gel to give (20S)-4-azido-21-hydroxy-20-methylpregn-4-en-3-one acetate as a white solid (1.6 g, 50.1%), melting at 137°-138° C., with decomposition, after recrystallization from aqueous acetone. IR 2110, 1736, 1670, 1588 (m), 1254 cm$^{-1}$; MS (CI) 386 (3%, M +1 -N$_2$), 326 (100%, M+1−N$_2$−AcOH); $^1$H NMR (CDCl$_3$) δ 0.72 (3H, s, C$_{18}$-Me), 1.01 (d, C$_{22}$-Me), 1.14 (s, C$_{19}$-Me), 2.06 (s, Ac-Me), 3.02 (1H, dq, C$_6$-H), 3.77 (1H, dd, ½ C$_{21}$-CH$_2$), 4.08 (1H, dd, ½ C$_{21}$-CH$_2$).

EXAMPLE 11

(20S)-4-Amino-21-hydroxy-20-methylpregn-4-en-3-one 21-Acetate

A stirred mixture of (20S)-4-azido-21-hydroxy-20-methylpregn-4-en-3-one acetate (1.4 g, 3.39 mmole), triphenylphosphine (1.08 g), tetrahydrofuran (25 mL) and water (7 mL) was heated at reflux temperature under argon for 18 hours. The solvents were removed from the cooled reaction and the residue was purified by flash chromatography to give (20S)-4-amino-21-hydroxy-20-methylpregn-4-en-3-one acetate (1.1 g, 84%). IR 3470, 3366, 1732, 1674, 1618, 1584, 1254 cm$^{-1}$; MS (CI) 388 (100%, M+1), 328 (70% M+1−AcOH); $^1$H NMR (CDCl$_3$) δ 0.72 (3H, s, C$_{18}$-Me), 1.00 (d, C$_{22}$-Me), 1.14 (s, C$_{19}$-Me), 2.04 (s, Ac-Me), 3.43 (2H, v br, NH$_2$), 3.76 (1H, dd, ½ C$_{21}$-CH$_1$), 4.07 (1H, dd, ½ C$_{21}$-CH$_1$). This compound has the following structure:

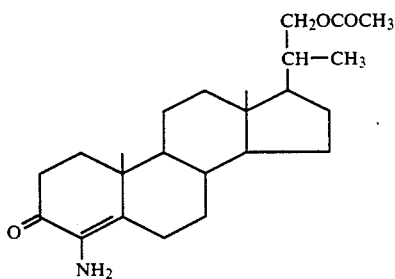

EXAMPLE 12

(20S)-21-Hydroxy-20-methylpregn-4-en-3-one Benzoate

A solution of (20S)-21-hydroxy-20-methylpregn-4-en-3-one (8.0 g, 24.2 mmole) in dichloromethane (200 mL) was cooled in an ice-water bath and treated sequentially with triethylamine (3.69 mL, 26.6 mmole) and benzoyl chloride (3.09 mL, 26.6 mmole) and stirred for 16 hours at room temperature. After the reaction mixture was diluted with dichloromethane (200 mL), it was extracted with ether, dried over magnesium sulfate and filtered and the filtrate was concentrated to a solid which was purified by flash chromatography to give (20S)-21-hydroxy-20-methylpregn-4-en-3-one benzoate (9.4 g, 89.5%) melting at 193°–195° C. after recrystallization from acetone. IR 1716, 1676, 1614 (m), 1284 cm$^{-1}$; MS (CI) 435 (100%, M+1), 313 (70%, M+1−PhCOOH); $^1$H NMR (CDCl$_3$) δ 0.77 (3H, s, C$_{18}$-Me), 1.04 (d, C$_{22}$-Me), 1.19 (s, C$_{19}$-Me), 4.05 (1H, dd, ½ C$_2$-CH$_2$), 4.34 (1H, dd, ½ C$_{21}$-CH$_2$), 5.72 (1H, s, C$_4$-H), 7.45 (2H, t), 7.56 (1H, t), 8.04 (2H, dd).

EXAMPLE 13

(20S)-4,5-Epoxy-21-hydroxy-20-methylpreqnan-3-one Benzoate

A solution of (20S)-21-hydroxy-20-methylpregn-4-en-3-one benzoate (8.9 g, 20.5 mmole) in methanol (80 mL) and dichloromethane (80mL) was cooled to 15° C. and treated sequentially with 30% hydrogen peroxide (5.0 mL) and sodium hydroxide (1.09 g) in water (6.7 mL). After 4 hours at room temperature, the product was isolated from the reaction mixture by the same procedure as described in Example 9 to give (20S)-4,5-epoxy-21-hydroxy-20-methylpregnan-3-one benzoate (1.6 g, 17.3%). IR 1720, 1280 cm$^{-1}$; MS (CI) 451 (95%, M+1), 329 (100%, M+1−PhCOOH); $^1$H NMR (CDCl$_3$) δ 0.76 (3H, s, C$_{18}$-Me), 1.13 (d, C$_{22}$-Me), 1.16 (s, C$_{19}$-Me), 2.98+3.04 (1H, s +s. C$_4$-H), 4.04 (1H, dd, ½ C$_{21}$-CH$_2$), 4.32 (1H, dd, ½ C$_{21}$-CH$_2$), 7.46 (2H, t), 7.57 (1H, t), 8.04 (1H, dd).

EXAMPLE 14

If the procedures as described in Examples 1 to 3 are repeated using the appropriate starting materials, the following compounds are obtained:

(20S)-4-Amino-21-hydroxy-20-methylpregn-4-en-3-one benzoate
4-Amino-17β-(hydroxymethyl)androst-4-en-3-one.
(20S)-4-Amino-20-hydroxypregn-4-en-3-one.
(20R)-4-Amino-20-hydroxypregn-4-en-3-one.
(20S)-4-Amino-20-hydroxypregna-4,16-dien-3-one.
(20R)-4-Amino-20-hydroxypregna-4,16-dien-3-one.
(20S)-4-Amino-20,21-dihydroxypregn-4-en-3-one.
4-Amino-21-hydroxypregn-4-en-3-one.
(20S)-4-Amino-21-methoxy-20-methylpregn-4-en-3-one.
(20R)-4-Amino-21-methoxy-20-methylpregn-4-en-3-one.
(20S)-4-Amino-21-(phenylmethoxy)-20-methylpregn-4-en-3-one.
(20R)-4-Amino-21-(phenylmethoxy)-2--methylpregn-4-en-3-one.
(20S)-4-Amino-21-[(4-chlorophenyl)methoxy]-20-methylpregn-4-en-3-one.
(20S)-4-Amino-21-[(4-methylphenyl)methoxy]-20-methylpregn-4-en-3-one.
(20S)-4-Amino-21-ethoxy-20-methylpregn-4-en-3-one.
(20S)-4-Amino-21-(2-phenylethoxy)-20-methylpregn-4-en-3-one

What is claimed is:

1. A compound of the formula:

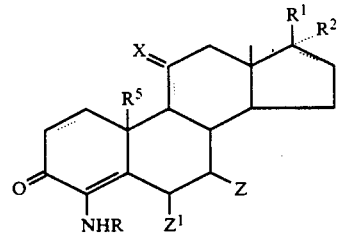

wherein R is hydrogen or C$_{1-4}$ alkyl; R$^1$ is C$_{2-6}$ alkanoyl, —(C$_{1-6}$ alkyl)-OZ$^2$, —(C$_{2-6}$ alkyl)—(OZ$^2$)$_2$ or —A—C-(O)—Y; Z$^2$ is hydrogen, C$_{1-6}$ alkyl, phenyl-(C$_{1-4}$ alkyl), (Y$^1$-substituted phenyl)-(C$_{1-4}$ alkyl), C$_{1-6}$ alkanoyl, benzoyl or Y$^1$-substituted benzoyl wherein Y$^1$ is methyl, halogen or methoxy; A is absent or is present as an alkylene of 1 to 6 carbon atoms; Y is —OH, —O(C$_{1-6}$ alkyl) or —NR$^3$R$^4$; R$^2$ is hydrogen or R$^1$ and R$^2$ can be combined to give —O—CH$_2$CH$_2$CH$_2$—; R$^3$ and R$^4$ are each independently hydrogen, C$_{1-6}$ alkyl, C$_{3-6}$ cycloalkyl or they can be combined to give —(CH$_2$)$_n$— wherein n is 4 to 6; R$^5$ is hydrogen or methyl; X is O or (H)(H); Z is hydrogen or C$_{1-6}$ alkyl; Z$^1$ is hydrogen or methylene; and each of the dotted lines in the rings indicates the optional presence of a double bond with the proviso that a 9,11-double bond can only be present when X is (H)(H) and the proviso that, when a 16,17-double bond is present, then R$^2$ is absent.

2. A compound according to claim 1 which has the formula:

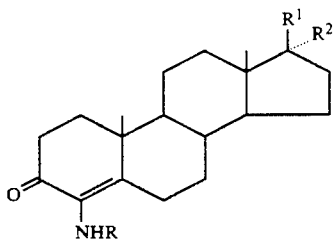

wherein R is hydrogen or $C_{1-4}$ alkyl; $R^1$ is $C_{2-6}$ alkanoyl, —CH(CH$_3$)—CH$_2$OZ$_2$, —CH(CH$_3$)—COO(C$_{1-6}$ alkyl) or —C(O)—NR$^3$R$^4$; $R^2$ is hydrogen or $R^1$ and $R^2$ can be combined to give —O—CH$_2$CH$_2$CH$_2$—; $Z^2$ is hydrogen, $C_{1-6}$-alkyl or $C_{1-6}$ alkanoyl; $R^3$ and $R^4$ are each independently hydrogen, $C_{1-6}$ alkyl, $C_{3-6}$ cycloalkyl or they can be combined to give —(CH$_2$)$_n$—wherein n is 4 to 6.

3. A compound according to claim 2 which has the formula:

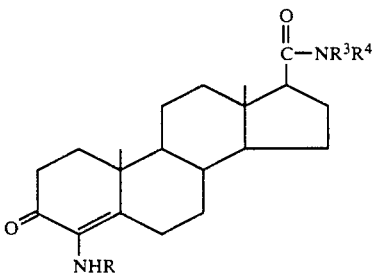

wherein R is hydrogen or $C_{1-4}$ alkyl; $R^3$ and $R^4$ are each independently hydrogen, $C_{1-6}$ alkyl, $C_{3-6}$ cycloalkyl or they can be combined to give —(CH$_2$)$_n$—wherein n is 4 to 6.

4. A compound according to claim 3 which has the formula:

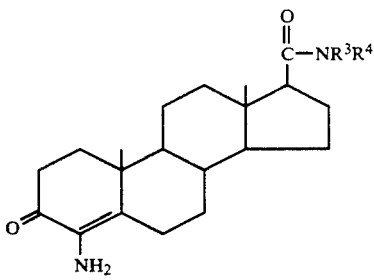

wherein $R^3$ and $R^4$ are each independently hydrogen or $C_{1-6}$ alkyl

5. A compound according to claim 4 which is 4-amino-N-(1,1-dimethylethyl)-3-oxoandrost-4-ene-17β-carboxamide 6. A compound according to claim 4 which is 4-amino-N,N-bis(1-methylethyl)-3-oxoandrost-4-ene-17β-carboxamide.

7. A compound according to claim 1 which has the formula:

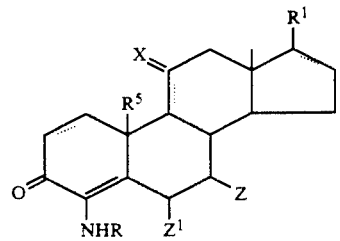

wherein R is hydrogen or $C_{1-4}$ alkyl; $R^1$ is —(C$_{1-6}$ alkyl)-OZ$^2$ or —(C$_{2-6}$ alkyl)—(OZ$^2$)$_2$; $Z^2$ is hydrogen, $C_{1-6}$ alkyl, phenyl-(C$_{1-4}$ alkyl), (Y$^1$-substituted phenyl)-(C$_{1-4}$ alkyl), $C_{1-6}$ alkanoyl, benzoyl or Y$^1$-substituted benzoyl wherein Y$^1$ is methyl, halogen or methoxy; $R^5$ is hydrogen or methyl; X is O or (H)(H); Z is hydrogen or $C_{1-6}$ alkyl; $Z^1$ is hydrogen or methylene; and each of the dotted lines in the rings indicates the optional presence of a double bond with the proviso that a 9,11-double bond can only be present when X is (H)(H).

8. A compound according to claim 7 which has the formula:

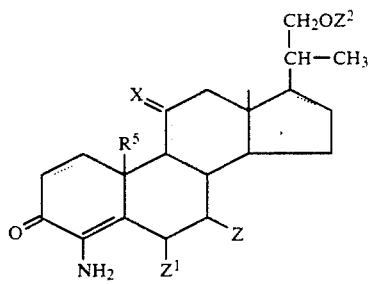

wherein $Z^2$ is hydrogen, $C_{1-6}$ alkyl, phenyl-(C$_{1-4}$ alkyl), (Y$^1$-substituted phenyl)-(C$_{1-4}$ alkyl), $C_{1-6}$ alkanoyl, benzoyl or Y$^1$-substituted benzoyl wherein Y$^1$ is methyl, halogen or methoxy; $R^5$ is hydrogen Or methyl; Z is hydrogen or $C_{1-6}$ alkyl; $Z^1$ is hydrogen or methylene; and each of the dotted lines in the rings indicates the optional presence of a double bond.

9. A compound according to claim 7 which is (20S)-4-amino-21-hydroxy-20-methylpregn-4-en-3-one.

* * * * *

UNITED STATES PATENT AND TRADEMARK OFFICE
CERTIFICATE OF CORRECTION

PATENT NO.  : 5,120,840
DATED       : June 9, 1992
INVENTOR(S) : Phillip M. Weintraub, Joseph P. Burkhart, Thomas R. Blohm, It is certified that error appears in the above-identified patent and that said Letters Patent is hereby corrected as shown below:

Column 2, line 24, "(H))H)" should read -- (H) (H) --.
Column 3, line 36, "oxoandrost4" should read -- oxoandrost-4- --.
Column 6, line 8, "Fiese," should read -- Fieser --.
Column 6, line 24, "procedure" should read -- procedure. --.
Column 9, line 20, " hexane40%" should read -- hexane - 40% --.
Column 9, line 64, " hexane30%" should read -- hexane - 30% --.
Column 11, line 36, "$C_{21}$-CHhd 2)," should read -- $C_{21}$-$CH_2$), --.
Column 12, line 66, "20methylpregn" should read -- 20-methylpregn --.
Column 14, line 30, "198°14 199°C." should read -- 198°-199°C.--.
Column 16, line 26, "-methylpregnan-" should read -- methylpregnan --.
Column 16, line 49-50, "epoxy21" should read -- epoxy-21 --.
Column 17, line 17, "$C_{21}$-$CH_1$)" should read -- $C_{21}$-$CH_2$) --.
Column 17, line 18, "$C_{21}$-$CH_1$)" should read -- $C_{21}$-$CH_2$) --.
Column 17, line 53, "$C_2$" should read -- $C_{21}$ --.
Column 17, line 56, "methylpreqnan" should read -- methylpregnan --.
Column 18, line 2, "($CDCl_33$)" should read -- ($CDCl_3$) --.
Column 18, line 26, "-2--" should read -- -20- --.
Column 20, line 39, 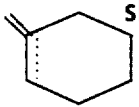 should read 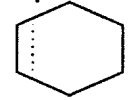

Signed and Sealed this

Fifth Day of October, 1993

Attest:

BRUCE LEHMAN

Attesting Officer          Commissioner of Patents and Trademarks